United States Patent [19]

Stoltefuss et al.

[11] Patent Number: 4,791,122

[45] Date of Patent: Dec. 13, 1988

[54] CIRCULATION ACTIVE NOVEL 5-ARYLDIHYDROPYRIDINES

[75] Inventors: Jürgen Stoltefuss, Haan; Rainer Gross, Wuppertal; Matthias Schramm, Cologne, all of Fed. Rep. of Germany; Günter Thomas, Garbagnate, Italy; Michael Kayser, Hagen; Bernd Pelster, St. Augustin, both of Fed. Rep. of Germany

[73] Assignee: Bayer Aktiengesellschaft, Leverkusen, Fed. Rep. of Germany

[21] Appl. No.: 816,916

[22] Filed: Jan. 8, 1986

[30] Foreign Application Priority Data

Jan. 22, 1985 [DE] Fed. Rep. of Germany ....... 3501855

[51] Int. Cl.$^4$ .................... A61K 31/44; A61K 31/455
[52] U.S. Cl. .................................. 514/344; 514/352; 514/355; 546/286; 546/312; 546/315; 546/316; 546/322
[58] Field of Search ............... 546/312, 286, 316, 322, 546/315; 514/355, 344, 352

[56] References Cited

U.S. PATENT DOCUMENTS 4,532,248 7/1985 Franckowirk et al. ............. 514/222

Primary Examiner—Mary C. Lee
Assistant Examiner—Zinna Northington
Attorney, Agent, or Firm—Sprung Horn Kramer & Woods

[57] ABSTRACT

5-Aryl-1,4-dihydropyridines of the formula

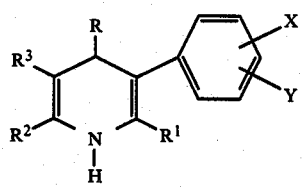

in which
R
  represents cycloalkyl,
  heteroaryl or
  aryl which is optionally substituted by at least one substituent independently selected from the group consisting of halogen, nitro, hydroxyl, amino, carboxyl, alkoxycarbonyl, cyano, acyl, acyloxy, acylthio, by alkyl, alkyloxy, alkylthio or alkylsulphonyl, each of which is optionally substituted by one or more halogens, by aryl which is optionally substituted by alkyl, alkoxy, halogen or nitro, or optionally by the group $-Z-CH_2-R^4$,
where
Z represents oxygen or sulphur, and
$R^4$
  represents cycloalkyl,
  heteroaryl or
  aryl which is optionally substituted by halogen, cyano, nitro, hydroxyl, carboxyl, alkoxycarbonyl or by alkyl or alkoxy, each of which is optionally substituted by one or more halogens,
$R^1$ and $R^2$
  are identical or different and
  represent straight-chain or branched alkyl which is optionally substituted by aryl, carboxyl, alkoxycarbonyl or by hydroxyl,
$R^3$
  represents nitro, cyano or
  the group

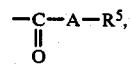

where
A represents oxygen, sulphur or $-N-R^6$,
$R^6$ represents hydrogen, phenyl or alkyl,
and where
$R^5$
  represents hydrogen,
  cycloalkyl or
  a hydrocarbon radical which is optionally interrupted in the chain by one or more carbonyl groups and/or sulphur and/or oxygen atoms and is optionally substituted by halogen, nitro, cyano, hydroxyl, mercapto, carboxyl, alkoxycarbonyl, aryl, acyloxy, acylthio, heteroaryl or by an amino group, the amino group carrying one or two identical or different substituents from the group comprising phenyl, alkyl or aralkyl,
X and Y
  are identical or different and
  represent hydrogen,
  alkyl, alkoxy or alkoxycarbonyl,
  halogen, hydroxyl, nitro, carboxyl, cyano or trifluoromethyl or trifluoromethoxy, or physiologically acceptable salts thereof, are active on the cardiovascular system.

16 Claims, No Drawings

CIRCULATION ACTIVE NOVEL 5-ARYLDIHYDROPYRIDINES

The present invention relates to 5-aryl-1,4-dihydropyridines, to a process for their preparation and to their use in medicaments, in particular in medicaments having effects on the circulation.

It has already been disclosed that certain 1,4-dihydropyridines have interesting pharmacological properties (F. Bossert, W. Vater "Die Naturwissenschaften" 58, 578 (1971)). As a rule, the known active compounds are esters of 1,4-dihydropyridine-3,5-dicarboxylic acids.

The invention now relates to 5-aryl-1,4-dihydropyridines of the general formula I

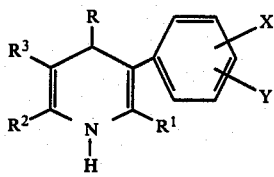

in which
R
represents cycloalkyl (3–7C atoms), heteroaryl or
aryl (6, 10C atoms) which is optionally substituted by one or more identical or different substituents such as halogen, nitro, hydroxyl, amine, carboxyl, alkoxycarbonyl (up to 6C atoms), cyano, acyl, acyloxy, acylthio (all up to 10C atoms), by alkyl, alkyloxy, alkylthio or alkylsulphonyl (each up to 8C atoms), each of which is optionally substituted by one or more halogens, by aryl (6, 10C atoms) which is optionally substituted by alkyl, alkoxy (each up to 4C atoms), halogen or nitro, or optionally by the group $-Z-CH_2-R^4$
where
Z represents oxygen or sulphur, and
$R^4$
represents cycloalkyl (3–7C atoms), heteroaryl or
aryl (6, 10C atoms) which is optionally substituted by halogen, cyano, nitro, hydroxyl, carboxyl, alkoxycarbonyl (up to 6C atoms) or by alkyl or alkoxy (each up to 8C atoms), each of which is optionally substituted by one or more halogens,
$R^1$ and $R^2$
are identical or different and
represent straight-chain or branched alkyl (up to 6C atoms) which is optionally substituted by aryl (6, 10C atoms), carboxyl, alkoxycarbonyl (up to 6C atoms) or by hydroxyl,
$R^3$
represents nitro, cyano or
the group

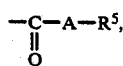

where
A represents oxygen, sulphur or $-N-R^6$,
$R^6$ represents hydrogen, phenyl or alkyl (up to 4C atoms),
and where
$R^5$
represents hydrogen,
cycloalkyl (3–7C atoms), or
a straight-chain or branched, saturated or unsaturated, hydrocarbon radical (up to 12C atoms) which is optionally interrupted in the chain by one or more carbonyl groups and/or sulphur and/or oxygen atoms and is optionally substituted by halogen, nitro, cyano, hydroxyl, mercapto, carboxyl, alkoxycarbonyl (up to 4C atoms), aryl (6, 10C atoms), acyloxy, acylthio (all up to 6C atoms), heteroaryl or by an amino group, the amino group carrying one or two identical or different substituents from the group comprising phenyl, alkyl (up to 3C atoms) or aralkyl (7–10C atoms),
X and Y
are identical or different and
represent hydrogen,
alkyl, alkoxy or alkoxycarbonyl (each up to 6C atoms),
halogen, hydroxyl, nitro, carboxyl, cyano or trifluoromethyl or trifluoromethoxy,
and to their physiologically acceptable salts.

The preferred compounds of the general formula I are those in which
R
represents cycloalkyl (4–7C atoms),
thienyl, pyridyl, furyl, benzoxadiazolyl, or
phenyl which is optionally substituted by up to three identical or different substituents such as fluorine, chlorine, bromine, nitro, hydroxyl, carboxyl, cyano, alkoxycarbonyl (up to 4C atoms), acetyl, acetyloxy, benzoyl, benzoyloxy, or alkyl, alkoxy, alkylthio or alkylsulphonyl (each up to 6C atoms) each of which is optionally substituted by one or more fluorine atoms, by phenyl which is optionally substituted by methyl, ethyl, methoxy, fluorine, chlorine or nitro, or optionally by the group $-Z-CH_2-R^4$,
where
Z represents oxygen or sulphur, and
$R^4$
represents cycloalkyl (4–7C atoms),
thienyl, furyl or pyridyl, or
phenyl which is optionally substituted by fluorine, chlorine, bromine, cyano, nitro, hydroxyl, carboxyl, alkoxycarbonyl (up to 4C atoms) or by alkyl or alkoxy (up to 6C atoms) each of which is optionally substituted by one or more fluorine atoms,
$R^1$ and $R^2$
are identical or different and
represent staight-chain or branched alkyl (up to 5C atoms) which is optionally substituted by phenyl, carboxyl, hydroxyl or alkoxycarbonyl (up to 4C atoms),
$R^3$ represents nitro, cyano or the group

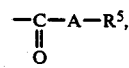

where
A represents oxygen, and where
$R^5$
represents hydrogen,
cycloalkyl (4–7C atoms), or a straight-chain or branched, saturated or unsaturated hydrocarbon radical (up to 10C atoms) which is optionally interrupted in the chain by one to three oxygen and/or sulphur atoms and is optionally substituted by one or more of fluorine, chlorine, bromine, nitro, cyano, hydroxyl, carboxyl, alkoxycarbonyl (up to 2C atoms), phenyl, benzylmethylamino, pyridyl, furyl or thienyl, X and Y
are identical or different and
represents hydrogen,
alkyl, alkoxy or alkoxycarbonyl (each up to 4C atoms),
fluorine, chlorine, bromine, hydroxyl, nitro, carboxyl, cyano or
trifluoromethyl, trifluoromethoxy, and their physiologically acceptable salts.

The particularly preferred compounds are those of the general formula I in which
R
represents cyclopentyl or cyclohexyl,
thienyl, furyl or pyridyl, or
phenyl which is optionally substituted by one or two identical or different substituents such as fluorine, chlorine, nitro, carboxyl, alkoxycarbonyl (up to 2C atoms), cyano, phenyl, or alkyl, alkyloxy, alkylthio or alkylsulphonyl (each up to 4C atoms) which is optionally substituted by one or more fluorine atoms, or optionally by the group —Z—CH$_2$—R$^4$,
where
Z represents oxygen or sulphur, and
R$^4$
represents cyclopentyl or cyclohexyl,
thienyl, furyl or pyridyl, or
phenyl which is optionally substituted by fluorine, chlorine, cyano, nitro, hydroxyl, carboxyl, alkoxycarbonyl (up to 2C atoms) or by alkyl or alkyloxy (up to 4C atoms) each of which is optionally substituted by one or more fluorine atoms,
R$^1$ and R$^2$
are identical or different and
represent straight-chain or branched alkyl (up to 4C atoms) which is optionally substituted by phenyl, carboxyl or alkoxycarbonyl (up to 3C atoms),
R$^3$
represents nitro or
the group

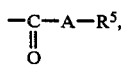

where
A represents oxygen,
R$^5$
represents cyclopentyl, cyclohexyl or
a straight-chain or branched, saturated or unsaturated hydrocarbon radical (up to 8C atoms) which is optionally interrupted in the chain by one or two oxygen and/or sulphur atoms and is optionally substituted by one or more of fluorine, chlorine, nitro, cyano, hydroxyl or pyridyl,
X and Y
are identical or different and
represent hydrogen,
fluorine, chlorine, hydroxyl, nitro, cyano, trifluoromethyl, trifluoromethoxy or
alkyl, alkoxy, alkoxycarbonyl (each up to 2C atoms),
and their physiologically acceptable salts.

Possible physiologically acceptable salts are salts of the compounds according to the invention with inorganic and organic acids or bases. Examples which may be mentioned are: salts with acids such as hydrohalic acids, sulphuric acid, phosphoric acid, acetic acid, maleic acid, citric acid, fumaric acid, tartaric acid, lactic acid, benzoic acid and salts with bases such as ammonia, alkali metal and alkaline earth metal hydroxides, or organic amines.

The compounds according to the invention are new and have valuable pharmacological properties. They affect the contractility of the heart and can thus be used to control cardiovascular disorders. Thus the new 5-aryl-1,4-dihydropyridines represent an enrichment of pharmacy.

The substances according to the invention, of the general formula I in which R$^1$-R$^6$, A, X, Y and Z have the abovementioned meaning, are obtained when (A) aldehydes of the general formula II

in which R has the abovementioned meaning, and keto compounds of the general formula III

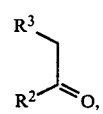

in which R$^2$ and R$^3$ have the abovementioned meaning, are reacted with keto compounds of the general formula IV

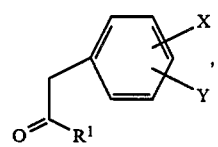

in which R$^1$, X and Y have the abovementioned meaning, and ammonia or a suitable ammonium salt, where appropriate in the presence of water or inert organic solvents, or when (B) aldehydes of the general formula II are reacted with keto compounds of the general formula III and enamines, where appropriate prepared in situ, of the general formula V

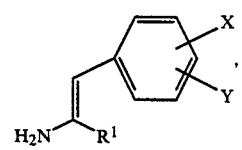

in which R$^1$, X and Y have the abovementioned meaning, where appropriate in the presence of water or inert organic solvents, or when (C) aldehydes of the general formula II are reacted with keto compounds of the general formula IV and enamines of the general formula VI

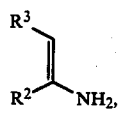
(VI)

in which $R^2$ and $R^3$ have the abovementioned meaning, where appropriate in the presence of water or inert organic solvents, or when (D) ylidene compounds of the general formula VII

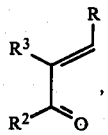
(VII)

in which R, $R^2$ and $R^3$ have the abovementioned meanings, are reacted with keto compounds of the general formula IV and ammonia or a suitable ammonium salt, where appropriate in the presence of water or inert organic solvents, or when (E) keto compounds of the general formula III are reacted with ylidene compounds of the general formula VIII

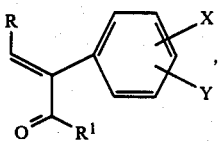
(VIII)

in which R, $R^1$, X and Y have the abovementioned meaning, and ammonia or a suitable ammonium salt, where appropriate in the presence of water or inert organic solvents, or when (F) ylidene compounds of the general formula VII are reacted with enamines of the general formula V, where appropriate in the presence of water or inert organic solvents, or when (G) enamines of the general formula VI are reacted with ylidene compounds of the general formula VIII, where appropriate in the presence of water or inert organic solvents.

Depending on the nature of the starting materials used, it is possible to represent the reactions by the following equations:

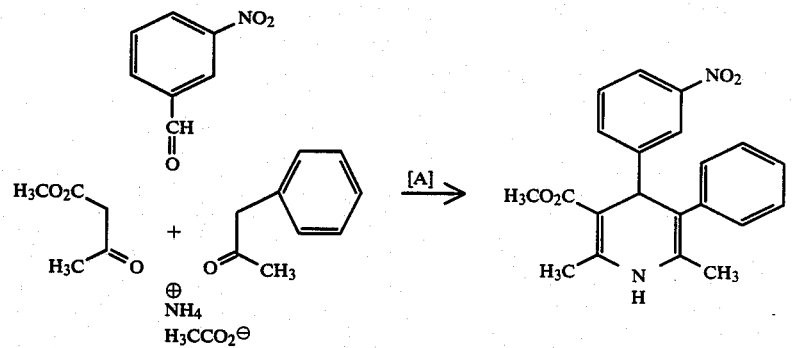

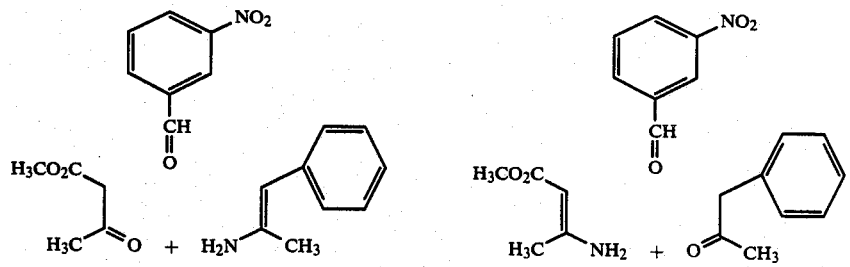

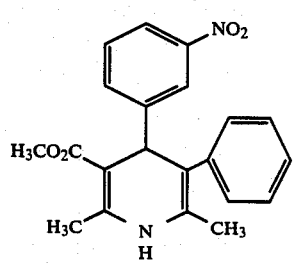

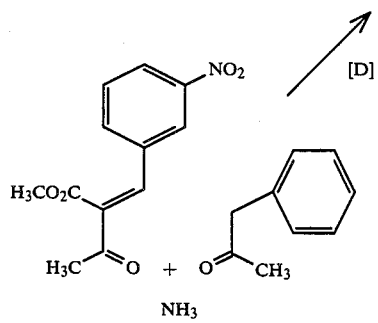 [D]

-continued

[E] 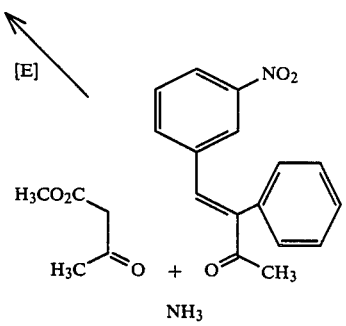

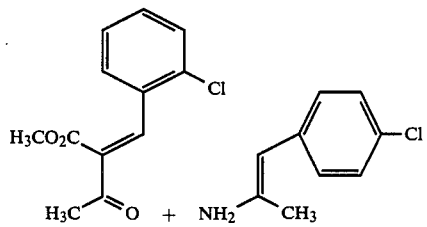

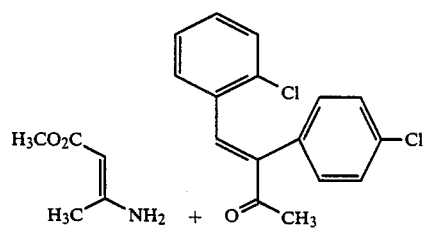

[F] [G]

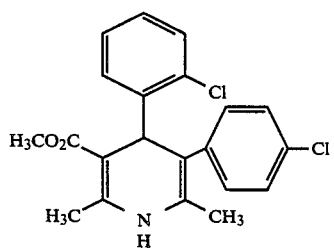

Depending on the choice of the starting substances, the compounds according to the invention can exist in stereoisomeric forms which are either related as image and mirror image (enantiomers) or are not related as image and mirror image (diastereomers). The present invention relates to both the antipodes and the racemic forms as well as the mixtures of diastereomers. The racemic forms can, as can the diastereomers, be separated in a known manner into the stereoisomerically homogeneous constitutents (see, for example, E. L. Eliel, Stereochemistry of Carbon Compounds, McGraw Hill, 1962).

The aldehydes (II) which are used are known or can be prepared by methods known from the literature (see T. D. Harris and G. P. Roth, J. org. Chem. H 2004, 146 (1979); German Offenlegungsschrift (German published specification) No. 2,401,665; Mijano et al., Chem. Abstr. 59 (1963), 13929 c; E. Alder and H.-D. Becker, Acta Chem. Scand. 15, 849 (1961); E. P. Papadopoulos, H. A. Jarrar and C. Issidorides, J. Org. Chem. 31, 615 (1966).

Some of the keto compounds of the formula (III) are known or they can be prepared by known methods (see N. Levy and C. W. Scaife, J. Chem. Soc. (London) (1946) 1103; C. D. Hurd and M. E. Nilson, J. Org. Chem. 20, 927 (1955); D. Borrmann, "Umsetzung von Diketen mit Alkoholen, Phenolen und Mercaptanen" (Reaction of Diketene with Alcohols, Phenols and Mercaptans), in Houben-Weyl, Methoden der organischen Chemie (Methods of Organic Chemistry), Vol VII/4, 230 et seq. (1968); Y. Oikawa, K. Sugano and O. Yonemitsu, J. Org. Chem. 43, 2087 (1978).

The keto compounds of the formula IV are known or can be prepared by known methods (see H. G. Walker, C. R. Hauser, J. Am. Chem. Soc. 68, 1368, (1946); G. G. Smith, J. Am. Chem. Soc. 75, 1134 et seq. (1953).

The enamines of the formula V are known or can be prepared by known methods (see H. Ahlbrecht G. Rauchschwalbe, Tetrahedron Letters 51, 4897–4900 (1971).

The enamines of the formula VI are known or can be prepared by known methods (see S. A. Glickmann, A. C. Cope, J. Am. Chem. Soc. 67, 1017 (1945); H. Böhme, K.-H. Weisel, Arch. Pharm. 310, 30 (1977).

The ylidene compounds of the formula VII are known or can be prepared by known methods (see Organic Reactions XV, 204 et seq. (1967).

The ylidene compounds of the formula VIII are known or can be prepared by known methods (see J. F. Codington, E. Moseittig, J. Org. Chem. 17, 1023 (1952); W. Dilthey, B. Stallmann, Chem. Ber. 62, 1603 (1929).

Suitable ammonium salts may be salts of ammonia with inorganic or organic acids. The following may be mentioned as examples: halides, sulphates, hydrogensulphates, hydrogenphosphates, acetates, carbonates and hydrogencarbonates.

Suitable diluents for all process variants A to G are water or all inert organic solvents. These preferably include alcohols, such as ethanol, methanol and isopropanol, ethers, such as dioxane, diethyl ether, tetrahydrofuran, glycol monomethyl ether and glycol dimethyl ether, or glacial acetic acid, dimethylformamide, dimethyl sulphoxide, acetonitrile, pyridine and hexamethylphosphoric acid triamide. The process is preferably carried out with the addition of glacial acetic acid.

The reaction temperatures can be varied within a relatively wide range. In general, the reaction is carried out between 0° and 200° C., in particular between 10° and 150° C., but preferably at the boiling point of the particular solvent.

The reaction can be carried out under atmospheric pressure, but also under elevated pressure. In general, it is carried out under atmospheric pressure.

The above preparation processes are indicated merely for illustration, and the preparation of the compounds of the formula (I) is not restricted to these processes, but every modification of these processes can be used in the same manner for the preparation of the compounds according to the invention.

The ratio of the amounts of the reactants to one another is optional, but in general equimolar amounts are used. However, it has proved to be advantageous in process E to use the keto compound of the general formula III and the ammonia component, and in process G to use the enamines of the general formula VI, in up to 10-fold molar excess.

The compounds according to the invention show a valuable spectrum of pharmacological effects which could not have been predicted. They affect the contractility of the heart and the tone of smooth muscle. In addition, they have an inhibitory effect on lipoxygenase. Hence they can be used in medicaments for the treatment of cardiovascular disorders, for example for the treatment of hypertension, coronary heart disease, cardiac insufficiency and hypotension. Furthermore, they can be used for the treatment of cardiac arrhythmias, for reducing blood sugar, for reducing mucosal swelling and for affecting the salt and fluid balance.

The cardiovascular effects were found on isolated, perfused guinea-pig hearts. The hearts of albino guinea-pigs weighing 250 to 350 g are used for this purpose. The animals are sacrificed by a blow to the head, the thorax is opened, a metal cannula is tied into the exposed aorta, and the left atrium is opened. The heart with the lungs is dissected out of the thorax and attached via the aorta cannula to the perfusion apparatus while perfusion is in progress.

The lungs are excised at the lung roots. The perfusion medium used in Krebs-Henseleit solution (118.5 mmol/l NaCl, 4.75 mmol/l KCl, 1.19 mmol/l $KH_2PO_4$, 119 mmol/l $MgSO_4$, 25 mmol/l $NaHCO_3$, 0.013 mmol/l NaEDTA), the $CaCl_2$ in which being varied as required but being 1.2 mmol/l as a rule. 10 mmol/l glucose are added as a substrate to provide energy. The solution is filtered to remove particles before the perfusion. Carbogen (95% $O_2$, 5% $CO_2$) is passed through the solution to maintain the pH of 7.4. The hearts are perfused with a constant flow (10 ml/min) at 32° C. using a peristaltic pump.

In order to measure cardiac function, a fluid-filled latex balloon, which is connected via a fluid column to a pressure sensor, is introduced through the left atrium into the left ventricle, and the isovolumetric contractions are recorded on a rapid pen recorder (Opie, L., J. Physiol. 180 (1965) 529–541). The perfusion pressure is recorded using a pressure sensor which is connected with the perfusion system upstream of the heart. Under these conditions, a reduction in the perfusion pressure indicates coronary dilation, and an increase in the left-ventricular pressure amplitude indicates an increase in the contractility of the heart. The compounds according to the invention are infused in suitable dilutions into the perfusion system a short distance upstream of the isolated heart.

| Example No. | Change in the contraction amplitude ($10^{-7}$ g/ml substance) |
|---|---|
| 1 | +37% |
| 19 | +22% |

The new active compounds can be converted in a known manner into the customary formulations, such as tablets, capsules, coated tablets, pills, granules, aerosols, syrups, emulsions, suspensions and solutions, using inert, non-toxic, pharmaceutically suitable excipients or solvents, The therapeutically active compound should in each case be present in a concentration of about 0.5 to 90% by weight of the total mixture, that is to say amounts which suffice to achieve the dosage range indicated.

The formulations are prepared, for example, by extending the active compounds with solvents and/or excipients, optionally with the use of emulsifiers and/or dispersing agents, and, for example, when using water as a diluent, organic solvents can optionally be used as auxiliary solvents.

Examples of auxiliaries which may be mentioned are: water, non-toxic organic solvents, such as paraffins (for example petroleum fractions), vegetable oils (for example peanut/sesame oil), alcohols (for example ethyl alcohol and glycerol), glycols (for example propylene glycol and polyethylene glycol), solid excipients, such as, for example, natural rock powders (for example kaolins, aluminas, talc and chalk), synthetic rock powders (for example highly disperse silica and silicates), sugars (for example sucrose, lactose and glucose), emulsifiers (for example polyoxyethylene fatty acid esters, polyoxyethylene fatty alcohol ethers alkyl-sulphonates and arylsulphonates), dispersing agents (for example lignin, sulphite waste liquors, methylcellulose, starch and polyvinyl pyrrolidone) and lubricants (for example magnesium stearate, talc, strearic acid and sodium sulphate).

Administration is effected in the customary manner, preferably orally or parenterally, in particular perlingually or intravenously. In the case of oral administration, the tablets can, of course, also contain, in addition to the excipients mentioned, additives such as sodium citrate, calcium carbonate and dicalcium phosphate, together with various additional substances, such as starch, preferably potato starch, gelatine and the like. Furthermore, lubricants such as magnesium stearate, sodium lauryl sulphate and talc can also be used when making tablets. In the case of aqueous suspensions and/or elixirs which are intended for oral use, the active compounds can be mixed with various flavor-improving agents or colorants in addition to the abovementioned auxiliaries.

In the case of parenteral administration, solutions of the active compounds, employing suitable liquid excipients, can be used.

In general, it has proved advantageous, in the case of intravenous administration, to administer amounts of about 0.001 to 1 mg/kg, preferably about 0.01 to 0.5 mg/kg, of body weight to achieve effective results, and in the case of oral administration the dosage is about 0.01 to 20 mg/kg, preferably 0.1 to 10 mg/kg, of body weight.

Nevertheless, it can at times be necessary to deviate from the amounts mentioned, and in particular to do so as a function of the body weight of the experimental animal or of the nature of the administration method, but also because of the species of animal and its individual behavior towards the medicament, or the nature of the formulation of the medicament and the time or interval over which the administration takes place. Thus it can suffice in some cases to manage with less than the abovementioned minimum amount, while in other cases the upper limit mentioned must be exceeded. Where relatively large amounts are administered, it can be advisable to divide these into several individual administrations over the course of the day. The same dosage range is envisaged for administration in human medicine. In this connection, the above statements similarly apply.

PREPARATION EXAMPLES

EXAMPLE 1

4-(2-Benzyloxyphenyl)-1,4-dihydro-2,6-dimethyl-3-nitro-5-phenylpyridine

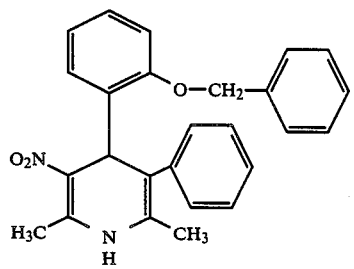

3 g (10 mmol) of 2-benzyloxybenzylidenenitroacetone in 15 ml of ethanol are heated under reflux with 1.34 g (10 mmol) of phenylacetone and 770 mg (10 mmol) of ammonium acetate for 1.5 hours. The mixture is cooled and concentrated. The residue from evaporation is taken up in ethyl acetate, and the solution is washed with water, dried and concentrated. The resulting residue from evaporation is purified through a column of volume 150 ml, stationary phase silica gel and mobile phase toluene/ethyl acetate 10:1. The pure fractions are combined, concentrated and crystallized using ether. 0.2 g of yellow crystals, of melting point 189° C., is obtained.

EXAMPLE 2

Methyl 4-(3-chlorophenyl)-1,4-dihydro-2,6-dimethyl-5-phenyl-pyridine-3-carboxylate

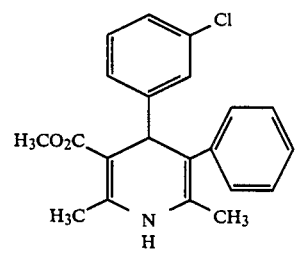

12.82 g (50 mmol) of 1-(3-chlorophenyl)-2-phenyl-3-oxo-1-butene in 80 ml of ethanol are heated to reflux with 11.5 g (100 mmol) of methyl β-aminocrotonate and 6 ml (100 mmol) of acetic acid overnight. 11.5 g of methyl β-aminocrotonate and 6 ml of acetic acid are added once more, and the mixture is heated under reflux for 24 hours. On cooling, crystals are produced, and these are filtered off with suction and washed with ethanol. For complete purification, they are passed through a silica gel column using toluene/ethyl acetate 20:1. 5.3 g of a colorless substance, of melting point 191° C., are obtained.

EXAMPLE 3

4-(3-Chlorophenyl)-1,4-dihydro-2,6-dimethyl-3-nitro-5-phenylpyridine

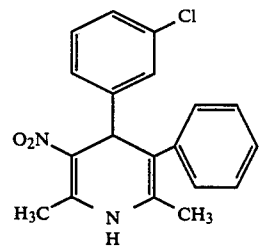

12.82 g (50 mmol) of 1-(3-chlorophenyl)-2-phenyl-3-oxo-1-butene in 75 ml of ethanol are heated under reflux with 5.15 g (50 mmol) of nitroacetone and 3.85 g (50 mmol) of ammonium acetate for 16 hours. A further 5.15 g of nitroacetone and 3.85 g of ammonium acetate are added and the mixture is boiled for 24 hours, and 5.15 g of nitroacetone and 3.85 g of ammonium acetate are added and the mixture is boiled for 24 hours. It is cooled and concentrated, the residue is taken up in ethyl acetate, and the solution is extracted by shaking twice with water, dried and concentrated.

Purification on a silica gel column using toluene/ethyl acetate 10:1. The pure fractions are collected and concentrated, and the residue is stirred with ether, and the product is filtered off with suction and washed with ether. 5.2 g of orange-colored crystals, of melting point 157°–60° C., are obtained.

EXAMPLE 4

4-(2-Chlorophenyl)-1,4-dihydro-2,6-dimethyl-3-nitro-5-phenylpyridine

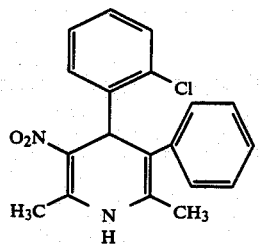

1.5 g (10 mmol) of 2-chlorobenzaldehyde are boiled with 1.03 g (10 mmol) of nitroacetone, 2.7 g (20 mmol) of phenylacetone and 0.7 g (10 mmol) of ammonium acetate in 20 ml of ethanol overnight. The mixture is concentrated, the residue is taken up in ethyl acetate, and the solution is washed with water, dried and concentrated. The residue from evaporation is purified on a silica gel column using toluene/ethyl acetate 10:1. The fractions containing product are collected and concentrated. The substance crystallizes using ether. It is filtered off with suction and washed with ether. 200 mg of orange-colored crystals, of melting point 232° C., are obtained.

The following substances are obtained in analogy to the above processes indicated in Examples 1 to 4:

EXAMPLE 5

4-(2-Benzyloxyphenyl)-5-(4-cyanophenyl)-1,4-dihydro-2,6-dimethyl-3-nitropyridine Melting point: 126° C.

EXAMPLE 6

Methyl 4-(3-chlorophenyl)-1,4-dihydro-5-(4-methoxyphenyl)-2,6-dimethylpyridine-5-carboxylate Melting point: 171° C.

EXAMPLE 7

6-Benzyl-4-(2-benzyloxyphenyl)-1,4-dihydro-2-methyl-3-nitro-5-phenylpyridine

Melting point: 173° C.

EXAMPLE 8

1,4-Dihydro-2,6-dimethyl-3-nitro-4,5-diphenylpyridine

Melting point: 187° C.

EXAMPLE 9

6-Benzyl-4-(2-chlorophenyl)-1,4-dihydro-2-methyl-3-nitro-5-phenylpyridine

Melting point: 177° C.

EXAMPLE 10

1,4-Dihydro-2,6-dimethyl-3-nitro-4-(2-nitrophenyl)-5-phenylpyridine

Melting point: 166°–170° C.

EXAMPLE 11

6-Benzyl-1,4-dihydro-2-methyl-3-nitro-4,5-diphenylpyridine

Melting point: 218° C.

EXAMPLE 12

Methyl 4-(2-chlorophenyl)-1,4-dihydro-2,6-dimethyl-5-phenylpyridine-3-carboxylate Melting point: 130° C.

EXAMPLE 13

Methyl 4-(2-chlorophenyl)-1,4-dihydro-2,6-dimethyl-5-phenylpyridine-3-carboxylate Melting point: 108° C.

EXAMPLE 14

4-(2-Fluorophenyl)-1,4-dihydro-2,6-dimethyl-5-phenyl-3-nitropyridine

Melting point: 206° C.

EXAMPLE 15

Methyl 4-(2-chlorophenyl)-1,4-dihydro-2-methoxycarbonylmethyl-6-methyl-5-phenylpyridine-3-carboxylate Melting point: 163° C.

EXAMPLE 16

Methyl 6-benzyl-1,4-dihydro-2-methyl-4,5-diphenylpyridine-3-carboxylate

Melting point: 184° C.

EXAMPLE 17

4-(2-Chlorophenyl)-6-ethyl-1,4-dihydro-2-methyl-3-nitro-5-phenylpyridine

Melting point: 195° C.

EXAMPLE 18

1,4-Dihydro-2,6-dimethyl-3-nitro-5-phenyl-4-(2-trifluoromethylphenyl)pyridine

Melting point: 206° C.

EXAMPLE 19

1,4-Dihydro-2,6-dimethyl-3-nitro-4-(3-nitrophenyl)-5-phenylpyridine

Melting point: 157° C.

EXAMPLE 20

Methyl 1,4-dihydro-2,6-dimethyl-4-(3-nitrophenyl)-5-phenyl-3-carboxylate

Melting point: 152° C.

EXAMPLE 21

Methyl 1,4-dihydro-2,6-dimethyl-4-(2-nitrophenyl)-5-phenylpyridine-3-carboxylate Melting point: 180° C.

EXAMPLE 22

Ethyl 4-(3-chlorophenyl)-2-ethoxycarbonylmethyl-1,4-dihydro-6-methyl-5-phenylpyridine-3-carboxylate Melting point: 129°–132° C.

EXAMPLE 23

1,4-Dihydro-2,6-dimethyl-3-nitro-5-phenyl-4-(3-trifluorophenyl)pyridine

Melting point: 162° C.

EXAMPLE 24

1,4-Dihydro-2,6-dimethyl-3-nitro-5-phenyl-4-(4-trifluoromethylmercaptophenyl)pyridine Melting point: 162° C.

EXAMPLE 25

4-Cyclohexyl-1,4-dihydro-2,6-dimethyl-3-nitro-5-phenylpyridine

Melting point: 195°–97° C.

EXAMPLE 26

4,5-Bis(4-chlorophenyl)-1,4-dihydro-2,6-dimethyl-3-nitropyridine

Melting point: 115°–116° C.

EXAMPLE 27

1,4-Dihydro-2,6-dimethyl-3-nitro-5-phenyl-4-thienyl-2-pyridine

Melting point: 157°–58° C.

EXAMPLE 28

1,4-Dihydro-4-(4-methoxyphenyl)-2,6-dimethyl-5-nitro-3-phenylpyridine

Melting point: 181° C.

EXAMPLE 29

Methyl 1,4-dihydro-2,6-dimethyl-5-phenyl-4-(2-trifluoromethylphenyl)pyridine-3-carboxylate $R_f$ 0.51

Merck TLC aluminum roll, mobile phase toluene/ethyl acetate in the ratio by volume 4:1.

Melting point: 143° C.

EXAMPLE 30

4-(4-Hydroxy-3-methoxyphenyl)-1,4-dihydro-2,6-dimethyl-5-phenyl-3-nitropyridine $R_f$ value: 0.1

Melting point: 227° C.

EXAMPLE 31

4-(4-Hydroxyphenyl)-1,4-dihydro-2,6-dimethyl-3-nitro-5-phenylpyridine $R_f$ value: 0.095

Melting point: 240° C.

EXAMPLE 32

Methyl 1,4-dihydro-4-(4-hydroxyphenyl)-2,6-dimethyl-5-phenylpyridine-3-carboxylate $R_f$ value: 0.66, mobile phase toluene/ethyl acetate in the ratio by volume 1:1.

EXAMPLE 33

1,4-Dihydro-2,6-dimethyl-4-(2-fluorophenyl)-5-(4-methoxyphenyl)-3-nitropyridine

Melting point: starts at 297° C.

EXAMPLE 34

4-(2-Chlorophenyl)-5-(4-cyanophenyl)-1,4-dihydro-2,6-dimethyl-3-nitropyridine

Melting point: 213° C.

It will be understood that the specification and examples are illustrative but not limitative of the present invention and that other embodiments within the spirit and scope of the invention will suggest themselves to those skilled in the art.

We claim:

1. A 5-phenyl-1,4-dihydropyridine or salt according to the formula

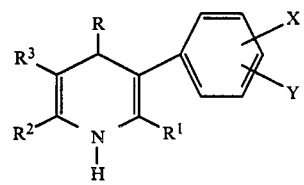

R
represents $C_4$–$C_7$-cycloalkyl,
thienyl, pyridyl, furyl, benzoxadiazolyl, or
phenyl which is unsubstituted or substituted by up to three substituents independently selected from the group consisting of fluorine, chlorine, bromine, nitro, hydroxyl, carboxyl, cyano, $C_1$–$C_4$-alkoxycarbonyl, acetyl, acetyloxy, benzoyl, benzoyloxy, or $C_1$–$C_6$-alkyl, $C_1$–$C_6$-alkoxy, $C_1$–$C_6$-alkylthio or $C_1$–$C_6$-alkylsulphonyl each of which is unsubstituted or substituted by one or more fluorine atoms, by phenyl which is unsubstituted or substituted by methyl, ethyl, methoxy, fluorine, chlorine or nitro, or optionally by the group —Z—$CH_2$—$R^4$, where Z represents oxygen or sulphur, and $R^4$ represents $C_4$–$C_7$-cycloalkyl,
thienyl, furyl or pyridyl, or
phenyl which is unsubstituted or substituted by fluorine, chlorine, bromine, cyano, nitro, hydroxyl, carboxyl, $C_1$–$C_4$-alkoxycarbonyl or by $C_1$–$C_6$-alkyl or $C_1$–$C_6$-alkoxy each of which is unsubstituted or substituted by one or more fluorine atoms, $R^1$ and $R^2$
are identical or different and
represent staight-chain or branched $C_1$–$C_5$-alkyl which is unsubstituted or substituted by phenyl, carboxyl, hydroxyl or $C_1$–$C_4$-alkoxycarbonyl, $R^3$ represents nitro, cyano or the group $$-\underset{\underset{O}{\|}}{C}-A-R^5,$$

where
A represents oxygen, and where
$R^5$
represents hydrogen,
$C_4$-$C_7$-cycloalkyl, or
a hydrocarbon radical with 1 to 10C atoms X and Y
are identical or different and
represent hydrogen,
$C_1$-$C_4$-alkyl, $C_1$-$C_4$-alkoxy or $C_1$-$C_4$-alkoxycarbonyl,
fluorine, chlorine, bromine, hydroxyl, nitro, carboxyl, cyano or
trifluoromethyl or trifluoromethoxy.

2. A 5-phenyl-1,4-dihydropyridine or salt according to claim 1, in which
R
represents cyclopentyl or cyclohexyl,
thienyl, furyl or pyridyl, or
phenyl which is unsubstituted or substituted by one to two substituents independently selected from the group consisting of fluorine, chlorine, nitro, carboxyl, $C_1$-$C_2$-alkoxycarbonyl, cyano, phenyl, or $C_1$-$C_4$-alkyl, $C_1$-$C_4$-alkyloxy, $C_1$-$C_4$-alkylthio or $C_1$-$C_4$-alkylsulphonyl which is unsubstituted or substituted by one or more fluorine atoms, or optionally by the group —Z—$CH_2$—$R^4$,
where
Z represents oxygen or sulphur, and
$R^4$ represents cyclopentyl or cyclohexyl,
thienyl, furyl or pyridyl, or
phenyl which is unsubstituted or substituted by fluorine, chlorine, cyano, nitro, hydroxyl, carboxyl, $C_1$-$C_2$-alkoxycarbonyl or by $C_1$-$C_4$-alkyl or $C_1$-$C_4$-alkyloxy each of which is unsubstituted or substituted by one or more fluorine atoms,
$R^1$ and $R^2$
are identical or different and
represent straight-chain or branched $C_1$-$C_4$-alkyl which is unsubstituted or substituted by phenyl, carboxyl or $C_1$-$C_3$-alkoxycarbonyl,
$R^3$
represents nitro or
the group $$-\underset{\underset{O}{\|}}{C}-A-R^5,$$

where
A represents oxygen,
$R^5$
represents cyclopentyl, cyclohexyl or
a hydrocarbon radical with up to 8C atoms,
X and Y
are identical or different and
represent hydrogen,
fluorine, chlorine, hydroxyl, nitro, cyano,
trifluoromethyl, trifluoromethoxy or
$C_1$-$C_2$-alkyl, $C_1$-$C_2$-alkoxy or $C_1$-$C_2$-alkoxycarbonyl.

3. A compound according to claim 1, wherein such compound is 4-(2-chlorophenyl)-1,4-dihydro-2,6-dimethyl-3-nitro-5-phenylpyridine of the formula

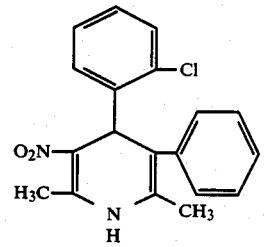

or a physiologically acceptable salt thereof.

4. A compound according to claim 1, wherein such compound is 4-(2-benzyloxyphenyl)-5-(4-cyanophenyl)-1,4-dihydro-2,6-dimethyl-3-nitropyridine of the formula

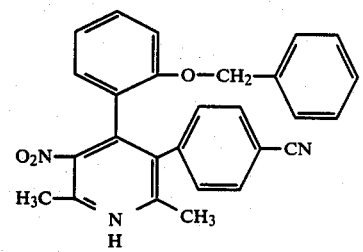

or a physiologically acceptable salt thereof.

5. A compound according to claim 1, wherein such compound is 1,4-dihydro-2,6-dimethyl-3-nitro-4,5-diphenylpyridine of the formula

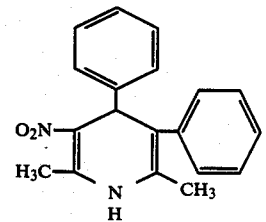

or a physiologically acceptable salt thereof.

6. A compound according to claim 1, wherein such compound is 4-(2-fluorophenyl)-1,4-dihydro-2,6-dimethyl-5-phenyl-3-nitropyridine of the formula

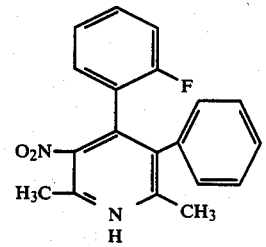

or a physiologically acceptable salt thereof.

7. A compound according to claim 1, wherein such compound is 1,4-dihydro-2,6-dimethyl-3-nitro-5-phenyl-4-thienylpyridine of the formula

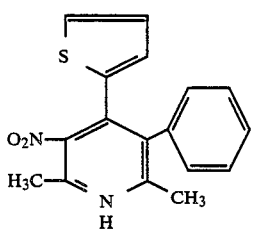

or a physiologically acceptable salt thereof.

8. A composition active for combating cardiac insufficiency and hypotension comprising an amount effective therefor of a compound or salt according to claim 1 in admixture with a diluent.

9. A unit dose of a composition according to claim 8 in the form of a tablet, capsule or ampule.

10. A method of combating cardiac insufficiency and hypotension which comprises administering to a patient in need thereof an amount effective therefor of a compound or salt according to claim 1.

11. The method according to claim 10, wherein such compound is
4-(2-chlorophenyl)-1,4-dihydro-2,6-dimethyl-3-nitro-5-phenylpyridine,
4-(2-benzyloxyphenyl)-5-(4-cyanophenyl)-1,4-dihydro-2,6-dimethyl-3-nitropyridine,
1,4-dihydro-2,6-dimethyl-3-nitro-4,5-diphenylpyridine,
4-(2-fluorophenyl)-1,4-dihydro-2,6-dimethyl-5-phenyl-3-nitropyridine or
1,4-dihydro-2,6-dimethyl-3-nitro-5-phenyl-4-thienylpyridine,
or a physilogically acceptable salt thereof.

12. A 5-phenyl-1,4-dihydropyridine or salt according to claim 1, in which $R^3$ represents nitro.

13. A 5-phenyl-1,4-dihydropyridine or salt according to claim 1, in which
$R^3$ represents the group

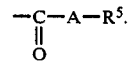

14. A composition for the treatment of hypertension, coronary heart disease or cardiac arrhythmia, for reducing mucosa swelling, for reducing blood sugar and for affecting the salt and fluid balance, comprising an amount effective therefor of a compound or salt according to claim 13 in admixture with a diluent.

15. A unit dose of a composition according to claim 14 in the form of a tablet, capsule of ampule.

16. A method of combating hypertension, coronary heart disease and cardiac arrhythmia, for reducing blood sugar and for affecting the salt and fluid balance, which comprises a method of combating cardiac insufficiency and hypotension which comprises administering to a patient in need thereof an amount effective therefor of a compound or salt according to claim 13.

* * * * *

UNITED STATES PATENT AND TRADEMARK OFFICE
CERTIFICATE OF CORRECTION

PATENT NO. : 4,791,122

DATED : December 13, 1988

INVENTOR(S) : Jürgen Stoltefuss, et al

It is certified that error appears in the above-identified patent and that said Letters Patent is hereby corrected as shown below:

| | |
|---|---|
| Title Page, under "U.S. Patent Documents" | Correct spelling of --Frankowiak-- |
| Col. 1, line 32 | Delete "amine" and substitute --amino-- |
| Col. 7, line 49 | Correct spelling of --constituents-- |
| Col. 7, line 57 | Delete "Alder" and substitute --Adler-- |
| Col. 20, line 6 | Correct spelling of --physiologically-- |
| Col. 20, line 24 | Before "ampule", delete "of" and substitute --or-- |

Signed and Sealed this

Fifth Day of December, 1989

Attest:

JEFFREY M. SAMUELS

Attesting Officer     Acting Commissioner of Patents and Trademarks